United States Patent
Oomori et al.

(12)

(10) Patent No.: US 6,423,320 B1
(45) Date of Patent: *Jul. 23, 2002

US006423320B1

(54) INHIBITOR OF IMMUNOGLOBULIN E ANTIBODY PRODUCTION

(75) Inventors: Hitoshi Oomori, Okayama; Yoichi Ooiso, Higashiosaka; Ryosuke Sugihara, Osaka, all of (JP)

(73) Assignee: Tayca Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,424

(22) PCT Filed: Jan. 5, 1998

(86) PCT No.: PCT/JP98/00029

§ 371 (c)(1),
(2), (4) Date: Aug. 19, 1998

(87) PCT Pub. No.: WO98/30224

PCT Pub. Date: Jul. 16, 1998

(30) Foreign Application Priority Data

Jan. 7, 1997 (JP) ............................................. 9-013125

(51) Int. Cl.⁷ ..................... A61K 39/108; A61K 39/02; A61K 39/00; A61K 45/00; A61K 31/70
(52) U.S. Cl. ................................ 424/259.1; 424/234.1; 424/184.1; 424/278.1; 424/282.1; 424/831; 514/23; 514/54; 514/826; 514/885

(58) Field of Search ........................ 424/184.1, 234.1, 424/259.1, 831, 278.1, 282.1, 236.1; 514/826, 885, 23, 54

(56) References Cited

U.S. PATENT DOCUMENTS

| 4,755,381 A | * | 7/1988 | Cryz et al. ..................... 424/92 |
| 4,870,053 A | * | 9/1989 | Zalisz et al. ..................... 514/8 |
| 5,527,904 A | * | 6/1996 | Nakanishi et al. ........ 536/123.1 |
| 5,739,014 A | * | 4/1998 | Nakanishi et al. .......... 435/101 |
| 5,760,213 A | | 6/1998 | Ooiso et al. ............. 536/123.1 |
| 5,989,874 A | * | 11/1999 | Nakanishi et al. .......... 435/101 |

FOREIGN PATENT DOCUMENTS

| EP | 238739 | * | 9/1987 |
| EP | 0308279 | | 3/1989 |
| WO | 90/13600 | * | 11/1990 |
| WO | 96/39155 | * | 12/1996 |

OTHER PUBLICATIONS

English Abstract for EP 0308279.

* cited by examiner

*Primary Examiner*—S. Devi
(74) *Attorney, Agent, or Firm*—Millen, White, Zelano & Branigan, P.C.

(57) ABSTRACT

A polysaccharide and fragments thereof derived from *Klebsiella oxytoca* or *Klebsiella pneumonia* inhibit the IgE antibody production and response and, therefore, are useful in the prophylaxis and/or treatment of type I allergy-related diseases.

7 Claims, No Drawings

INHIBITOR OF IMMUNOGLOBULIN E ANTIBODY PRODUCTION

FIELD OF THE INVENTION

This invention relates to a composition that inhibits the immunoglobulin E (IgE) antibody production and response in vivo. It also relates to the use of such composition in the prophylaxis and treatment of type I allergy-related diseases.

BACKGROUND OF THE INVENTION

Allergies are classified into I to IV types, and the type I allergy is frequently observed and brings about bronchial asthma, some urticarialy, allergic rhinitis, anaphylaxis etc. Type I allergy is a biological reaction in which IgE antibody is involved, and the mechanism of this type of allergy consists of (1) production of IgE antibody by immunization of a living body with an antigen, (2) binding of the IgE antibody via IgE receptor to mast cells and basophils, (3) upon re-invasion of the antigen, it binds to the previous IgE antibody bound to the surfaces of mast cells and basophils, thereby forming cross-linkages between IgE receptors on these cells, (4) via various reactions such as inflow of Ca ion, chemical mediators such as histamine, leukotriene, eosinophil chemotactic factor of anaphylaxis (ECF-A), platelet activating factor (PAF) are released to develop the allergic symptom.

The majority of known anti-allergy agents are antihistamine agents or inhibitors of the release of chemical mediators. It is expected that the type of drugs whose working mechanism is based on the inhibition of the earliest step of occurrence of type I allergy, i.e. production of IgE antibody, can be a superior drug against this type of allergies, but as such a type of drug, there is no drug with sufficient efficacy. IPD (IPD-1151T, Suplatast Tosylate) is the only anti-allergy agent having some ability to-inhibit the production of IgE antibody (Bio Industry, Vol. 13, No. 12, pp. 42–50 (1996)), and this compound has extremely weak inhibitory action on the production of IgE antibody.

SUMMARY OF THE INVENTION

It is, therefore, an object of the present invention to provide a composition which inhibits the IgE antibody production and response and which is more potent than known agents or compositions in the anti-IgE antibody production inhibitory activity,.

According to the present invention, the above and other objects may be accomplished by providing a composition for inhibiting the IgE antibody production and response comprising a capsule component of Klebsiella oxytoca or Klebsiella pneumoniae, a fragment thereof produced by the treatment of said capsule component with an acid, a base or a reducing agent.

DETAILED DESCRIPTION OF THE INVENTION

Particularly preferable *Klebsiella oxytoca* is *Klebsiella oxytoca* strain TNM3 (FERM BP-4669, deposited with the National Institute of Bioscience Human-Technology, Agency of Industrial Science and Technology, the Ministry of International Trade and Industry, Japan) or mutants thereof. Particularly preferable *Klebsiella pneumoniae* is *Klebsiella pneumoniae* strain K19 (Michel Beurret et al., "Structural investigation of the capsular polysaccharide from Klebsiella K19 by chemical and N.M.R. analyses", Carbohydrate Research, 157:13–25 (1986)) or mutants thereof.

These mutants can be generated by known mutagenesis means including exposure of *Klebsiella oxytoca* strain TNM3 or *Klebsiella pneumoniae* strain K19 to radiation such as ultraviolet light, X-ray etc. or contacting it with chemical mutagens such as ethyl methane sulfonate (EMS), N-methyl-N'-nitro-N-nitrosoguanidine (MNNG) etc.

The presence or absence and the degree of inhibitory activity on IgE antibody production, of the capsule component of these microorganisms or a fragment thereof obtainable by treating the capsule component with acid, base or a reducing agent can be easily measured in the methods described below.

*Klebsiella oxytoca* strain TNM3 and *Klebsiella pneumoniae* strain K19 have polysaccharides as a capsule component having the following linkage mode and constituent molar ratio. That is, the capsule component is a polysaccharide having a repeating unit represented by the following formula:

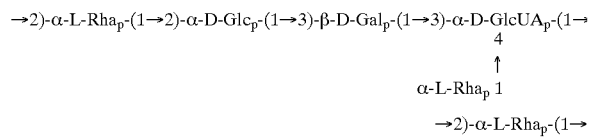

wherein L-Rha is an L-rhamnose residue, D-Gal is a D-galactose residue, D-Glc is a D-glucose residue, and D-GlcUA is a D-glucuronic acid reside, and the numerical values in the small brackets indicate the positions of the glycoside linkage, and the proportions of respective monosaccharide residues constituting the polysaccharide chain in terms of moles are 0.8 to 1.2 for

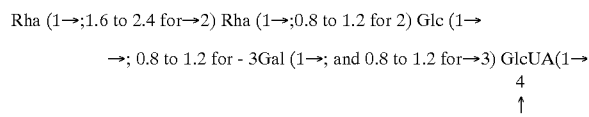

The above polysaccharide of fragments thereof produced by the treatment of the polysaccharide with an acid, a base or a reducing agent exhibit a potent inhibitory activity against IgE antibody production and response in vivo. Therefore, they are useful in the prophylaxis and treatment of type I allergy-related diseases.

The capsular polysaccharide component is prepared by culturing the microorganism in a medium, wet sterilizing or ultrasonificating the microorganism to release the capsular component into the medium, centrifuging the culture to give a supernatant, ultrafiltering the supernatant through a membrane having a fractionation molecular weight of $1 \times 10^3$ such as available from Millipore. The polysaccharide occurs in the retainant fraction.

The product resulting from the fragmentation of the capsule component can be obtained by treating the capsule component with an acid, a base or a reducing agent. Further, the treatment with a reducing agent can also be carried out by adding ferrous sulfate and EDTA to the medium while the microorganism is cultured.

*Klebsiella oxytoca* strain TNM3 is particularly preferable in the present invention. Culture of microorganisms of the genus Klebsiella can be carried out generally according to the following method. That is, the medium for culture may be any medium insofar as the microorganisms of the genus Klebsiella can grow in it, and carbon and nitrogen sources, inorganic salts, and trace nutrient sources which are necessary for producing the desired capsule component are contained in it, and there is no other limitation to the medium.

The carbon source used may be e.g. glucose, lactose, maltose, xylose, mannitol, sucrose, rhamnose, arabinose, trehalose, raffinose etc. The nitrogen source used may be e.g. synthetic compounds such as nitrates, ammonium salts, urea etc., natural organic matter such as polypeptone, corn steep liquor, yeast extract, meat extract, delipidated soybean extract, peptide, amino acid etc. The inorganic salts used may be e.g. phosphates, potassium salts, sulfates, magnesium salts etc. The trace nutrient sources used may be e.g. yeast extract, various vitamins etc. As necessary, calcium salts, manganese salts etc. may be added to the medium.

The medium used may be a solid or liquid medium. If the liquid medium is used, stationary culture may be used, but shake culture or shake culture under aeration is more preferable to achieve the desired capsule component in higher yield. The pH of the medium during culture is not particularly limited inasmuch as the pH is suitable for growth of the microorganism and simultaneously does not prevent the target capsule component from being produced. However, the pH range of 4 to 8 is usually preferable. The culture temperature is not particularly limited, but usually 20 to 35° C. is preferable. The period of culture is suitably determined so as to maximize the production of the target capsule component, but 1 to 7 days are usually preferable.

The resulting culture itself can be used as an inhibitor of the production of IgE antibody after sterilization without purification. However, it is more preferable to remove the microorganism and to purify the desired capsule component. The removal of the microorganism can be carried out by releasing capsules from the microorganism by wet-sterilization, and subsequent centrifugation and/or filtration in a usual manner. After removal of the microorganism, the culture may be further subjected to purification procedures: that is, a water miscible organic solvent such as methanol, ethanol, isopropanol, acetone or the like is added to the culture to form precipitates which are then dissolved in water, dialyzed against water and the dialysate is dried by such means as air drying, drying in hot air, spray drying, drum drying, drying under reduced pressure, lyophilization etc. For purification, other methods may be carried out. For example, use can be made of ultrafiltration (e.g. a membrane with a cut off molecular weight of $1 \times 10^3$, manufacture by Millipore can be used for concentration) followed by drying the resulting concentrate, and as necessary, various kinds of column chromatography, such as ion exchange, gel filtration, and affinity and precipitation or salting-out with quaternary ammonium salts, precipitation with organic solvent etc. are also used.

The culture itself or the purified capsule component may be further subjected if desired to various treatments including addition of a reducing agent, acid or base hydrolysis, heating under pressure, ultrasonication etc. For acid or base hydrolysis, an acid such as sulfuric acid, hydrochloric acid etc. or a base is added preferably under regulated conditions to the culture after culturing the microorganism or to the capsule component purified as described above.

For culture, a reducing agent may be added to the medium to such a level as not to decrease the amount of capsule component produced in the medium. As the reducing agent, a combination of ferrous sulfate and/or ferrous chloride and EDTA is preferable.

The polysaccharides as the capsule component, or fragments obtained by treatment with acid, base or reducing agent, have an inhibitory activity on the production of IgE antibody, as described in the following test examples. Accordingly, these can be used as inhibitors of IgE antibody production or as agents for preventing or treating type I allergies. It was revealed that even after oral administration of 5 g/kg in an acute toxicity test on rat, the animal survived while the increase in weight of the animal was similar to that of the control animal, and further there were no abnormalities in the appearance and autopsy. Therefore, the safety of these components in oral administration is considered to be high.

EXAMPLES

Hereinafter, the present invention is described in more detail by reference to several typical examples and test examples, which however are not intended to limit the scope of the present invention.

Example 1

Culture of a Microorganism of the Genus Klebsiella and Recovery of Capsule Component 100 ml medium with the composition as shown in Table 1 was introduced into a 500 ml flask and wet-sterilized for 20 minutes by heating at 121° C. *Klebsiella oxytoca* TNM3 (FERM BP-4669) was cultured in a liquid medium with the composition shown in Table 2 under shaking for 3 days in a test tube and then inoculated via a loop of platinum into the medium of Table 1. The microorganism was subjected to reciproshake culture at 28° C. for 1 day with shaking at 110 strokes/min.

TABLE 1

| (Medium Composition (weight %)) | |
| --- | --- |
| glucose | 2% |
| polypeptone | 0.1% |
| potassium monohydrogen phosphate | 0.15% |
| magnesium sulfate, 7H$_2$O | 0.05% |
| vitamin B$_1$ | 0.0005% |
| biotin | 0.000006% |
| calcium pantothenate | 0.001% |
| nicotinamide | 0.0005% |
| pH | 6.5 |

TABLE 2

| (Medium Composition (weight-%)) | |
| --- | --- |
| glucose | 4% |
| polypeptone | 0.1% |
| potassium monohydrogen phosphate | 0.15% |
| magnesium sulfate, 7H$_2$O | 0.05% |
| vitamin B$_1$ | 0.0005% |
| biotin | 0.000006% |
| calcium pantothenate | 0.001% |
| nicotinamide | 0.0005% |
| pH | 7 |

The resulting culture, 400 ml, was inoculated into 15 L jar fermenter containing 8 L medium with the composition shown in Table 2 sterilized in the same manner as described above, and the microorganism was cultured for 95 hours under aeration at 5 L/min. with stirring at 28° C., during which the pH in the system was maintained at 7 with aq. 5 M NaOH. The stirring was 200 rpm for the first 24 hours of culture, then 400 rpm until 33 hours of culture, and then 700 rpm until 95 hours of culture.

The resulting culture was adjusted to pH 4.5 with 10% sulfuric acid and wet-sterilized by heating at 121° C. for 60 minutes to release the capsule component from the microorganism, and the majority of the microorganism was removed by centrifugation, and the supernatant was repeatedly filtered through a 0.45 µm membrane filter to remove the microorganism from it. The resulting filtrate was repeatedly subjected to ultrafiltration in a cross flow system until the remaining medium components were removed. For the ultrafiltration, an ultrafiltration membrane manufactured by Millipore (fractionation molecular weight: $1 \times 10^5$) was used. The concentrate which did not pass through the ultrafiltration membrane was lyophilized to give 21 g extract based on the capsule polysaccharides per liter of medium.

Example 2
Fragmentation of the Capsular Polysaccharides of the Microorganism of the Genus Klebsiella 10 g of the capsule component obtained in the same manner as in Example 1 was dissolved in a buffer adjusted to pH 4.5, then subjected to gentle acid-hydrolysis at 121° C. for 25 minutes, adjusted to pH 12.5 with 10 M sodium hydroxide, left at room temperature for 5 hours, and subjected to ultrafiltration in the cross-flow system (ultrafiltration membrane with a fractionation molecular weight of $1 \times 10^5$, manufactured by Millipore) repeatedly until the decomposed products were removed. The concentrate was desalted through cation exchange resin and adjusted to pH 6.8 with sodium hydroxide and lyophilized to give about 7 g product resulting from fragmentation of the capsule component.

Example 3
Culture of the Microorganism of the Genus Klebsiella in the Presence of Ferrous Sulfate and Recovery of the Fragmented Product The same procedure as in Example 1 was carried out until reciproshake culture. Then, the resulting culture, 400 ml, was inoculated into 10 L jar fermenter containing 6 L medium with the composition as shown in Table 3 sterilized in the same manner as in Example 1. The microorganism was cultured at 28° C. for 86 hours with stirring under aeration while maintaining the pH in the system at pH 7 with 5-M aq. NaOH, where the aeration rate was 3.6 L/min. for the first 21 hours of culture and 4.8 L/min. thereafter. The stirring was 250 rpm for the first 20 hours of culture, then 500 rpm until 36 hours of culture, and then 650 rpm until 86 hours of culture.

TABLE 3

| (Medium Composition (weight-%)) | |
| --- | --- |
| glucose | 2% |
| ammonium sulfate | 0.06% |
| potassium monohydrogen phosphate | 0.15% |
| magnesium sulfate, 7H$_2$O | 0.05% |
| ferrous sulfate, 7H$_2$O | 0.003% |
| EDTA 2Na, 2H$_2$O | 0.01% |
| vitamin B$_1$ | 0.0005% |
| biotin | 0.000006% |
| calcium pantothenate | 0.001% |
| nicotinamide | 0.0005% |
| pH | 7 |

The resulting culture was wet-sterilized by heating at 121° C. for 20 minutes, and the microorganism was removed by centrifugation. The resulting supernatant was repeatedly subjected to ultrafiltration in the cross-flow system until the remaining medium components etc. were removed. For the ultrafiltration, an ultrafiltration membrane manufactured by Millipore (fractionation molecular weight: $1 \times 10^5$) was used. The concentrate which did not pass the ultrafiltration membrane was lyophilized to give 9.6 g product based on fragments from the capsular polysaccharides per liter of medium.

Measurement of Inhibitory Activity on the Production of Antigen-specific Antibody 1. Preparation of Test Samples Each product obtained in the Examples above was dissolved in water at a concentration of 1 weight-%, and cation exchange resin was added to the resulting aqueous solution to convert counter ions in acid groups contained in the culture into hydrogen ions and then removed, and the filtrate was neutralized with sodium hydroxide to replace the counter ions by sodium ions. Thereafter, it was filtered through a membrane filter of 0.2 μm in pore size and then lyophilized. Each of the test samples was subjected to the following experiments.

Test Example 1
Measurement of Inhibitory Activity on the Production of Antigen-specific Antibody An 8 week-old male mouse (BDF1, 5 to 6 animals/group) was immunized by intraperitoneal injection of 0.2 ml physiological saline containing a mixture of 2 mg aluminum hydroxide as adjuvant and 10 μg TNP-KLH as antigen prepared by reacting keyhole limpet hemocyanin with trinitrophenol.

The fragment-based product from capsule polysaccharides, obtained in Example 3, was dissolved in physiological saline and 150 μl of the solution was subcutaneously administered into the back of the above BDF1 mouse at a dosage of 100 mg/kg. This administration was carried out 5 times in total on the day before immunization and 3 days after immunization. The control group was given physiological saline in place of the above polysaccharide solution. Whole blood was collected 10 days later and determined for the amount of anti-TNP-IgE antibody produced in it.

The determination of the amount of produced anti-TNP-IgE antibody was carried out according to the ELISA method reported by Ohomori, H., Immunol. Lett., 23: 251–256 (1990) as follows.

1. Preparation of Rat-derived Anti-mouse IgE Antibody-coated Plate

6HD5(r) (mouse IgE antibody derived from rat, manufactured by Yamasa Co., Ltd.) was diluted at a concentration of 20 μg/ml with A1 buffer of Table 4 below and put to a 96-well plate in an amount of 50 μL/well and left at 4° C. for 12 hours to be coated on it. The supernatant was removed and 250 μL of 0.2 weight-% BSA solution (bovine serum albumin) in Al buffer was added to each well and left at 4° C. for further 12 hours for blocking. The supernatant was removed, and the plate was used in the subsequent test.

TABLE 4

| (A1 buffer) | |
| --- | --- |
| disodium phosphate, 12H$_2$O | 2.1 g |
| monosodium phosphate, 2H$_2$O | 0.59 g |
| sodium azide | 0.96 g |
| magnesium chloride, 6H$_2$O | 0.195 g |
| sodium chloride | 5.6 g |
| distilled water | 960 ml |

2. Treatment of the Sample

The sample was diluted with 0.1 weight-% BSA solution in A2 buffer below at a concentration in such an suitable range as to enable the fluorescence measurement described below and then added in a volume of 50 μL to each well on the above plate, followed by being left at 4° C. for 12 hours for reaction. The supernatant was removed, and the plate was washed twice with 0.01 weight-% BSA solution in A2 buffer. Then 50 μl of TNP-β-galactosidase solution at a suitable concentration (about a few μg/ml) in 0.1 weight-% in A2 buffer of Table 5 below was added to each well and the plate was allowed to react at 4 ° C. for 4 hours. The supernatant was removed, and the plate was washed 3 times with 0.02 vol.-% TWEEN 20 (Polyoxyethylene-sorbitan monolaurate) in A2 buffer.

TABLE 5

| (A2 buffer) | |
| --- | --- |
| A1 buffer | 100 ml |
| sodium chloride | 1.25 g |

To each well was added 100 μl solution prepared by diluting a stock solution of 10 mg/ml of 4-MUG (methylumbelliferyl-β-D-galactoside) in DMF (diemthylformamide) 100-fold with 0.1 weight-% BSA solution in A1 buffer. After reaction at 37° C. for 45 minutes, the reaction was terminated by adding 100 μl of 0.1 M glycine buffer, pH 10.3 and then its fluorescence measurement (excitation wavelength of 365 nm, fluorescent wavelength 450 nm) was carried out.

All procedures described above were carried out under cooling on ice unless otherwise specified.

To prepare a calibration curve, the same operation was carried out using anti-TNP-IgE antibody at known concentrations.

The degree of inhibition of production of IgE antibody was calculated using the following equation. The results are shown in Table 6.

Degree of inhibition of IgE antibody production (%)=[(C−S)/C]× 100

(where C is the amount of anti-TNP-IgE antibody produced in the control, and S is the amount of anti-TNP-IgE antibody produced in the group given the sample.)

Test Example 2

The degree of inhibition of production of anti-TNP-IgE antibody was determined using the same procedure as in Test Example 1 except that the extracted capsular polysaccharides, obtained in Example 1, was used, and that whole blood was collected 9 days after immunization. The results are shown in Table 6.

Test Example 3

The degree of inhibition of production of anti-TNP-IgE antibody was determined using the same procedure as in Test Example 1 except that the fragmented product from capsule components, obtained in Example 2, was used, that the period of administration was from the day before immunization to 2 days after immunization, and that whole blood was collected 9 days after immunization. The results are shown in Table 6.

Test Example 4

Administration of the Culture After Antigen Inoculation

The degree of inhibition of production of anti-TNP-IgE antibody was determined using the same procedure as in Test Example 1 except that the fragmented product from capsule components, obtained in Example 2, was used, that the sample or physiological saline (control) was administered 4 times in total over 1 to 4 days after immunization and that whole blood was collected 9 days after immunization. The results are shown in Table 6.

Test Example 5

Oral Administration

The degree of inhibition of production of anti-TNP-IgE antibody was determined by the same procedure as in Test Example 1 except that the fragmented product from capsule components, obtained in Example 2, was dissolved in physiological saline and 150 μl of the solution was orally administered into a BDF1 mouse at a dosage of 100 mg/kg 4 times in total from the day before immunization to 3 days after immunization, and that whole blood was collected 9 days after immunization. The results are shown in Table 6.

Test Example 6

The degree of inhibition of production of anti-TNP-IgE antibody was determined by the same procedure as in Test Example 1 except that the fragmented product from capsular components, obtained in Example 2, was dissolved in physiological saline and 150 μl of the solution was subcutaneously administered into a BKF1 mouse at a dosage of 50 mg/kg 4 times in total from the day before immunization to 3 days after immunization, and that whole blood was collected 9 days after immunization. The results are shown in Table 6.

Results of Test Examples 1 to 6

The average amounts (μg/ml) of anti-TNP-IgE antibody and percents inhibition of production of the antibody, as determined for the test samples and the control in Test Examples 1 to 6, are summarized in Table 6 below.

TABLE 6

| | Dosage (mg/kg) | Administration route | Administration period | Amount of antibody produced | | Degree of inhibition (%) |
|---|---|---|---|---|---|---|
| | | | | Sample | Control | |
| Test Exam. 1 | 100 | Subcutaneous | Previous day to 3 days later | 4.5 | 18.0 | 75 |
| Test Exam. 2 | 100 | Subcutaneous | Previous day to 3 days later | 15.5 | 37.0 | 58 |
| Test Exam. 3 | 100 | Subcutaneous | Previous day to 2 days later | 4.9 | 16.5 | 70 |
| Test Exam. 4 | 100 | Subcutaneous | 1 day later to 4 days later | 0.7 | 6.6 | 89 |
| Test Exam. 5 | 100 | Oral | Days of administration to 3 days later | 6.9 | 10.5 | 34 |
| Test Exam. 6 | 50 | Subcutaneous | Days of administration to 3 days later | 2.12 | 2.86 | 26 |

As shown in the results of Test Examples 1 to 4, the subcutaneous administration of the capsule component from the microorganism of the genus Klebsiella or its fragmented product inhibits production of anti-TNP-IgE antibody at higher degrees of inhibition. As can be seen from Test Examples 1 to Test Example 4, the inhibitory effects of these components on production of IgE antibody are similar regardless of whether administration of these components was initiated before or after immunization with the antigen. This indicates that the use of these components as an inhibitor of production of IgE antibody is extremely advantageous. Further, as shown in the result of Test Example 5, the inhibitory effect on production of IgE antibody has been achieved even by oral administration. This indicates that these components, even in the form of an oral agent, can be used as an inhibitor of production of IgE antibody, and thus as an agent for preventing or treating type I allergies.

Test Example 7

Antigenicity Test

Serums obtained from the groups (each of 5 to 6 animals) of BDF1 mice used in Test Examples 2 and 3 were mixed in equal volumes. The antigenicity of these serums was examined using Passive Hemaggulutination method (tannic acid method) described on pages 125 to 126 in "Menekigaku. Jikken Nyumon" (Introduction to Experiments in Immunology) published by Gakkai Shuppan Center. As the positive control, a mixture of 100 μg ovalbumin and 2 mg aluminum hydroxide as adjuvant was injected intraperitoneally into an 8-week-old male BDF1 mouse and serum from blood collected 9 days later was used. As the negative control phosphate buffered saline was used in place of ovalbumin, and serum was obtained in the same operation. The results are shown in the following table.

TABLE 7

|  | Intact serum | 1/2-fold dilution | 1/4-fold dilution |
| --- | --- | --- | --- |
| Negative control | − | − | − |
| Positive control | + | + | + |
| Serum from Test Example 2 | − | − | − |
| Serum from Test Example 3 | − | − | − |

As shown in Table 7, no antigenicity was observed in the capsule component of the microorganism of the genus Klebsiella or in its fragmented product. Accordingly, inhibitor of production of IgE antibody of this invention is considered to be highly safe in this respect too.

Example 4

Culture of the Microorganism of the Genus Klebsiella and Recovery of Capsule Component 100 ml medium with the composition as shown in Table 8 was introduced into a 500 ml flask and wet-sterilized by heating at 121° C. for 20 minutes. The microorganism was inoculated via a loop of platinum into the medium and subjected to reciproshake culture at 28° C. for 3 days with shaking at 110 strokes/min. 100 ml medium with the composition as shown in Table 9 was introduced into a 500 ml flask and sterilized in the same manner as above, and 1 ml of the above culture was inoculated via a loop of platinum into the medium and subjected to reciproshake culture at 28° C. for 1 day with shaking at 110 strokes/min.

The resulting culture, 300 ml, was inoculated into 15 L jar fermenter containing 8 L medium with the composition shown in Table 10 sterilized in the same manner as described above, and then cultured for 96 hours at 28° C., where the medium was stirred at 200 rpm for the first 36 hours of culture and then at 400 rpm until 96 hours of culture. Aeration was carried out at 1.5 L/min. for the first 48 hours of culture and then at 4 L/min. until 96 hours of culture.

TABLE 8

| Medium Composition (weight-%) | |
| --- | --- |
| glucose | 2% |
| polypeptone | 0.1% |
| potassium monohydrogen phosphate | 0.1% |
| magnesium sulfate, $7H_2O$ | 0.05% |
| vitamin $B_1$ | 0.0005% |
| biotin | 0.000006% |
| calcium pantothenate | 0.001% |
| nicotinamide | 0.0005% |
| calcium carbonate | 1.0% |
| pH | 7 |

TABLE 9

| Medium Composition (weight-%) | |
| --- | --- |
| glucose | 2% |
| polypeptone | 0.15% |
| potassium monohydrogen phosphate | 0.15% |
| magnesium sulfate, $7H_2O$ | 0.05% |
| vitamin $B_1$ | 0.0005% |
| biotin | 0.000006% |
| calcium pantothenate | 0.001% |
| nicotinamide | 0.0005% |
| pH | 7 |

TABLE 10

| Medium Composition (weight-%) | |
| --- | --- |
| glucose | 4% |
| polypeptone | 0.2% |
| potassium monohydrogen phosphate | 0.15% |
| magnesium sulfate, $7H_2O$ | 0.05% |
| ferrous sulfate, $7H_2O$ | 0.003% |
| EDTA 2Na, $2H_2O$ | 0.1% |
| vitamin $B_1$ | 0.0005% |
| biotin | 0.000006% |
| calcium pantothenate | 0.001% |
| nicotinamide | 0.0005% |
| calcium carbonate | 1.5% |
| pH | 7 |

The resulting culture was wet-sterilized by heating at 121° C. for 20 minutes, and the microorganism was removed by centrifugation. The precipitates formed by the addition of acetone to the supernatant were washed with 70% aqueous acetone and then lyophilized whereby 19 g component containing fragments from capsular polysaccharides per 1 liter of medium was obtained.

For purification, 20 g of the resulting component was dissolved in 500 ml of 0.1 M citrate buffer, pH 4.5 and heated at 121° C. for 10 minutes under wet conditions and the insolubles were removed by centrifugation. The supernatant was passed through a 0.45 μm membrane filter and the filtrate was subjected repeatedly to ultrafiltration in the cross flow system until low molecular components etc. were removed. For the ultrafiltration, an ultrafiltration membrane manufactured by Millipore (fractionation molecular weight: $1 \times 10^4$) was used.

Sodium hydroxide was added at a concentration of 0.01 M to the concentrate which did not pass through the ultrafiltration membrane and then stirred at room temperature for 6 hours. The supernatant from which insoluble components were removed by centrifugation was subjected to ultrafiltration in the cross flow system repeatedly until low molecular components etc. were removed.

For the ultrafiltration, the ultrafiltration membrane manufactured by Millipore (fractionation molecular weight: $1 \times 10^4$) was used. The concentrate which did not pass through the ultrafiltration membrane was passed through cation exchange resin, then neutralized with 1 M sodium hydroxide, passed through a 0.2 μm membrane filter, and lyophilized whereby 8.0 g purified product was obtained.

Example 5

Low Molecular Weight Fragment #1

2 g of the product of Example 4 containing fragments from capsular polysaccharides was dissolved in 400 ml distilled water, and 0.04 g EDTA-2 Na and 0.04 g ferrous sulfate $7H_2O$ were added to it under vigorous stirring. 5 minutes later, the solution was adjusted to pH 1.5 with 5 M aq. HCl, then introduced into a dialysis membrane tube with a fractionation molecular weight of 10,000 and dialyzed until low molecular components were completely removed, and the dialysate was neutralized with 1 M aqueous sodium hydroxide and lyophilized.

The molecular weight was found to be 80,000 by HPLC.

Example 6

Low Molecular Weight Fragment #2

2 g of the product of Example 4 containing fragments from capsular polysaccharides was dissolved in 400 ml distilled water, and 0.8 9 EDTA-2 Na and 0.8 g ferrous sulfate $7H_2O$ were added to it under vigorous stirring. 30 minutes later, 0.8 g EDTA-2 Na and 0.8 g ferrous sulfate $7H_2O$ were further added to it under vigorous stirring. The solution was adjusted to pH 1.5 with 5 M aq. HCl, then introduced into a dialysis membrane tube with a fractionation molecular weight of 10,000 and dialyzed until low molecular components were completely removed, and the dialysate was neutralized with 1 M aqueous sodium hydroxide and lyophilized.

The molecular weight was found to be 15,000 by HPLC.

Test Example 8

An 8 week-old male mouse (BDF1, 7 to 8 animals/group) was immunized by intraperitoneal injection of 0.2 ml physiological saline containing a mixture of 7 μg of TNP-KLH and 1 mg aluminum hydroxide.

Each of the low molecular weight products #1 and #2 obtained above was dissolved in physiological saline and 150 μl of this solution was subcutaneously administered into the back of the above BDF1 mouse at a dosage of 100 mg/kg 4 times in total form the day before immunization to 2 days after immunization. For the control group, physiological saline was used in place of the above polysaccharide solution. 9 days later, blood was collected from the bottom of the eyes, and the degree of inhibition of production of anti-TNP-IgE antibody was determined.

The average amounts (μg/ml) of anti-TNP-IgE antibody produced and the degree of inhibition of production of the antibody, as determined for the samples and the control, are shown in the following Table 11.

TABLE 11

| Test fragment | Administration method | Administration period | Amount of antibody produced | | Degree of inhibition |
|---|---|---|---|---|---|
| | | | Sample | Control | (%) |
| #1 | Subcutaneous | Day before immunization to 2 days after immunization | 0.42 | 6.04 | 93 |
| #2 | Subcutaneous | Day before immunization to 2 days after immunization | 1.84 | 6.04 | 70 |

Test Example 9

An 8 week-old male mouse (BDF1, 8 to 9 animals/group) was immunized by intraperitoneal injection of 0.2 ml physiological saline containing a mixture of 7 μg of TNP-OVA and 1 mg aluminum hydroxide.

The product of Example 4 was dissolved in physiological saline and 150 μl of this solution was subcutaneously administered into the back of the above BDF1 mouse at a dosage of 100 mg/kg 4 times in total from the day before immunization to 2 days after immunization. For the control group, physiological saline was used in place of the above polysaccharide solution. 9 days later, blood was collected from the bottom of the eyes, and the degree of inhibition of production of anti-TNP-IgE antibody was determined.

The average amounts (ng/ml) of anti-TNP-IgE antibody produced and the degree of inhibition of production of the antibody, as determined for the sample and the control, are shown in the following Table 12.

TABLE 12

| Day of blood collection | Administration | Administration | Amount of antibody produced | | Degree of inhibition |
|---|---|---|---|---|---|
| (day) | method | period | Sample | Control | (%) |
| 9 | Subcutaneous | Day before immunization to 2 days after immunization | 9.53 | 20.85 | 54 |

Test Example 10

An 8 week-old male mouse (BDF1, 5 animals/group) was immunized by intraperitoneal injection of 0.2 ml physiological saline containing a mixture of 10 μg of TNP-KLH and 1 mg aluminum hydroxide. Further, the animal was subjected on day 21 after immunization to secondary immunization by intraperitoneal injection of 0.2 ml physiological saline containing a mixture of 3 μg of TNP-KLH and 1 mg aluminum hydroxide.

The product of Example 4 was dissolved in physiological saline and 150 μl of this solution was subcutaneously administered into the back of the above BDF1 mouse at a dosage of 100 mg/kg 4 times in total from the day before immunization to 2 days after immunization. For the control group, physiological saline was used in place of the above polysaccharide solution. 9 days later, blood was collected from the bottom of the eyes, and on day 6 after secondary immunization, whole blood was collected, and the degree of inhibition of production of anti-TNP-IgE antibody was determined.

The average amounts (μg/ml) of anti-TNP-IgE antibody produced and the degree of inhibition of production of the antibody, as determined for the sample and the control, are shown in the following Table 13.

TABLE 13

| Day of blood collection (day) | Administration method | Administration period | Amount of antibody produced | | Degree of inhibition (%) |
|---|---|---|---|---|---|
| | | | Sample | Control | |
| 9 | Subcutaneous | Day before first immunization to 2 days after first immunization | 3.7 | 20.85 | 54 |
| 27 | | | 24.3 | 52.3 | 53 |

Test Example 11

An 8 week-old male mouse (BDF1, 8 to 9 animals/group) was immunized by intraperitoneal injection of 0.2 ml physiological saline containing a mixture of 7 μg of TNP-KLH and 1 mg aluminum hydroxide. Further, the animal was subjected on day 21 after immunization to secondary immunization by intraperitoneal injection of 0.2 ml physiological saline containing a mixture of 3 μg of TNP-KLH and 1 mg aluminum hydroxide.

The product of Example 4 was dissolved in physiological saline and 150 μl of this solution was subcutaneously administered into the back of the above BDF1 mouse at a dosage of 100 mg/kg 5 times in total from the day before secondary immunization to 3 days after secondary immunization. For the control group, physiological saline was used in place of the above polysaccharide solution. 9 days later, blood was collected from the bottom of the eyes, and on day 6 after secondary immunization, whole blood was collected, and the degree of inhibition of production of anti-TNP-IgE antibody was determined. The average amounts (μg/ml) of anti-TNP-IgE antibody produced and the degree of inhibition of production of the antibody, as determined for the sample and the control, are shown in the following Table 14.

TABLE 14

| Day of blood collection (day) | Administration method | Administration period | Amount of antibody produced | | Degree of inhibition (%) |
|---|---|---|---|---|---|
| | | | Sample | Control | |
| 9 | Subcutaneous | Day before second immunization to 2 days after second immunization | 1.95 | 1.75 | 0 |
| 27 | | | 46.1 | 31.7 | 31 |

What is claimed is:

1. A method for prophylaxis and/or treatment of a type I allergic disease which comprises administering to a type I allergic patient a composition comprising an effective amount of an isolated capsule component of a microorganism selected from the group consisting of *Klebsiella oxytoca* and *Klebsiella pneumoniae,* or a molecule retained by an ultrafiltration membrane having a cut off molecular weight of $1\times10^5$ daltons, said molecule produced by the treatment of said capsule component with an acid, a base or a reducing agent and wherein said isolated capsule component is a polysaccharide having a repeating unit of the formula:

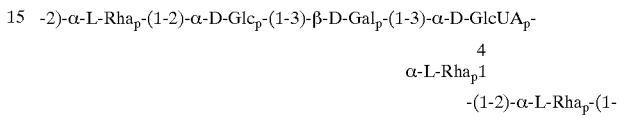

wherein L-Rha is an L-rhamnose residue, D-Gal is a D-galactose residue, D-Glc is a D-glucose residue, and D-GlcUA is a D-glucuronic acid residue, and the numerals indicate the positions of the glycoside linkages, said repeating unit being composed of respective monosaccharide residues in molar proportions of 0.8 to 1.2 for Rha(1-;1.6 to 2.4 for-2)Rha(1-; 0.8 to 1.2 for 2)Glc(1-; 0.8 to 1.2 for- -3Gal(1-; and 0.8 to 1.2 for-3)GlcUA(1-.
4

2. The method of claim 1, wherein said microorganism is *Klebsiella oxytoca* TNM3 FERM BP-4669.

3. The method of claim 1, wherein the composition is parenterally administered.

4. The method of claim 1, wherein the composition is orally administered.

5. The method of claim 1, wherein the microorganism is *Klebsiella pneumoniae* strain K19.

6. The method of claim 1, wherein the capsule component is administered in a dosage of about 50 to 100 mg/kg weight of the patient.

7. The method of claim 1, wherein the type I allergic disease is bronchial asthma, urticaria, allergic rhinitis or anaphylaxis.

* * * * *